United States Patent
Pavani

(10) Patent No.: US 10,184,901 B2
(45) Date of Patent: Jan. 22, 2019

(54) COMPUTATIONAL WAFER IMAGE PROCESSING

(71) Applicant: Exnodes Inc., Palo Alto, CA (US)

(72) Inventor: Sri Rama Prasanna Pavani, Palo Alto, CA (US)

(73) Assignee: Exnodes Inc., Fremont, CA (US)

(*) Notice: Subject to any disclaimer, the term of this patent is extended or adjusted under 35 U.S.C. 154(b) by 126 days.

(21) Appl. No.: 15/420,107

(22) Filed: Jan. 31, 2017

(65) Prior Publication Data

US 2017/0140517 A1 May 18, 2017

Related U.S. Application Data

(62) Division of application No. 14/532,036, filed on Nov. 4, 2014, now Pat. No. 9,696,265.

(51) Int. Cl.
*H04N 7/18* (2006.01)
*G01B 5/30* (2006.01)
(Continued)

(52) U.S. Cl.
CPC ..... *G01N 21/9501* (2013.01); *G01N 21/8851* (2013.01); *G01N 21/94* (2013.01);
(Continued)

(58) Field of Classification Search
CPC .................. G01N 21/9501; G06T 2207/30148
See application file for complete search history.

(56) References Cited

U.S. PATENT DOCUMENTS

| 2004/0008394 A1* | 1/2004 | Lange | G01S 7/4816 |
| | | | 359/237 |
| 2009/0110303 A1* | 4/2009 | Nishiyama | G06K 9/00228 |
| | | | 382/225 |

(Continued)

*Primary Examiner* — Rebecca A Volentine

(57) ABSTRACT

A method for designing a filter to image a feature on a surface, comprising: acquiring an image of said feature, with said image of feature comprising information from multiple points of said feature; generating a structural model of said feature by extracting predetermined properties of said feature from said image of feature; computing a scattering model for said feature from said structural model of said feature, with said scattering model for feature having information on scattered electromagnetic field from feature propagating in a plurality of scattering angles, wherein said scattered electromagnetic field from feature is generated by scattering of an electromagnetic radiation by said feature; acquiring an image of said surface, with said image of surface comprising information from multiple points of said surface; generating a structural model of said surface by extracting predetermined properties of said surface from said image of surface; computing a scattering model for said surface from said structural model of said surface, with said scattering model for surface having information on scattered electromagnetic field from surface propagating in a plurality of scattering angles, wherein said scattered electromagnetic field from surface is generated by scattering of an electromagnetic radiation by said surface; and computing said filter by combining said scattering model for feature and said scattering model for surface to achieve a predetermined filter performance metric, whereby said filter is designed to modulate scattered electromagnetic field from said feature and scattered electromagnetic field from said surface to image a feature on said surface. A system and method for recognizing a feature, comprising: acquiring an image of said feature using an imaging module, with said image of feature comprising information from multiple points of said (Continued)

feature; computing a feature spread function from scattering model of a previously known feature and transfer function of said imaging module, wherein said feature spread function represents a model of an image of said previously known feature; and comparing said image of feature with said feature spread function by computing a match metric between said image of feature and said feature spread function, whereby said match metric determines if said feature is similar to said previously known feature.

19 Claims, 7 Drawing Sheets

(51) Int. Cl.
    *G01N 21/95*     (2006.01)
    *G01N 21/88*     (2006.01)
    *G06K 9/00*     (2006.01)
    *G06K 9/46*     (2006.01)
    *G06K 9/62*     (2006.01)
    *G06K 9/60*     (2006.01)
    *G06T 7/00*     (2017.01)
    *G01N 21/94*     (2006.01)

(52) U.S. Cl.
    CPC ....... *G06K 9/0014* (2013.01); *G06K 9/00134* (2013.01); *G06K 9/46* (2013.01); *G06K 9/4609* (2013.01); *G06K 9/4661* (2013.01); *G06K 9/605* (2013.01); *G06K 9/6201* (2013.01); *G06K 9/624* (2013.01); *G06T 7/001* (2013.01); *G06T 7/0006* (2013.01); *G01N 2021/8883* (2013.01); *G01N 2201/12* (2013.01); *G06T 2207/10056* (2013.01); *G06T 2207/20016* (2013.01); *G06T 2207/30148* (2013.01)

(56) References Cited

U.S. PATENT DOCUMENTS

| | | | | |
|---|---|---|---|---|
| 2009/0297019 A1* | 12/2009 | Zafar | ........................ | G03F 1/84 382/145 |
| 2010/0004875 A1* | 1/2010 | Urano | ................ | G01N 21/4738 702/40 |
| 2011/0098992 A1* | 4/2011 | Van Beurden | .......... | G03F 7/705 703/2 |
| 2013/0057869 A1* | 3/2013 | Cotte | .................... | G02B 21/365 356/457 |
| 2013/0279294 A1* | 10/2013 | Angelsen | ................. | A61B 8/14 367/87 |
| 2015/0134286 A1* | 5/2015 | Chao | .................... | G01N 21/9501 702/82 |
| 2015/0369752 A1* | 12/2015 | Honda | ............... | G01N 21/8851 356/237.2 |
| 2016/0027157 A1* | 1/2016 | Naruse | ................... | H04N 9/045 382/167 |
| 2016/0117847 A1* | 4/2016 | Pandev | .................. | G06T 7/001 348/87 |
| 2017/0193643 A1* | 7/2017 | Naruse | .................. | H04N 5/232 |

* cited by examiner

COMPUTATIONAL WAFER IMAGE PROCESSING

CROSS-REFERENCE TO RELATED APPLICATIONS

This application is a divisional application of U.S. application Ser. No. 14/532,036, filed on Nov. 4, 2014. The contents of which are hereby incorporated by reference.

FIELD OF THE INVENTION

This invention relates generally to wafer image processing and more particularly to computational wafer image processing for use in wafer inspection.

BACKGROUND

Semiconductor wafers are used in the fabrication of integrated circuits (ICs) that drive modern electronic devices. The fabrication of ICs typically involve hundreds of process steps such as implantation, deposition, lithography, etching, and polishing. These process steps help in fabricating tiny (nanometer scale) structures on semiconductor wafers.

The abundance of modern electronic devices is primarily due to advances in the design and fabrication of ICs. These advances have increased processing power, memory capacity, and bandwidth in ICs. Remarkably, they have also reduced the cost of ICs. Advances in ICs are primarily made possible by node scaling and increase in wafer size. Node scaling refers to the decreasing sizes of component sizes in ICs. Increase in wafer size refers to increasing semiconductor wafer diameters. Together, node scaling and increase in wafer size allow semiconductor fabs to fabricate an increasing number of ICs on a single wafer, thereby reducing cost.

Production yield is another important factor that affects cost of ICs. Yield refers to the ratio of ICs that meet performance specifications to the total number of ICs. A lower yield results in an increased wastage of ICs, thereby increasing the cost of functional ICs. Semiconductor fabs strive to maximize yield in order to minimize cost. Maximizing yield is a challenging task because of the large number and complexity of process steps involved in IC fabrication. The determination of an IC to be non-functional at the end of fabrication does not necessarily point to the root-cause of what exactly went wrong in its exhaustive fabrication process. Knowing the root-cause is crucial to avoid propagation of fabrication errors to multiple wafers. In order to provide greater visibility into process steps, semiconductor fabs inspect wafers for abnormalities or defects after each significant process step. If a sudden increase in the number of defects is observed at a particular stage of fabrication process, steps are taken to immediately identify and eliminate the root cause of the observed defects so as to contain the undesirable yield impact due to excessive defects. First, properties of defects such as shape and size are determined. This defect information is used as an evidence to narrow down suspicious process steps that may be generating the defects. Parameters of the process steps thus identified are tuned to eliminate propagation of defects to multiple wafers.

The process of identifying root cause of defects is an exhaustive task involving multiple wafer inspection tools, resulting in an undesirable down time in semiconductor fabrication. In other words, production steps are often suspended until the root cause is identified an eliminated. This leads to a decrease in fabrication efficiency and an increase in cost. Typically, the process of identification of root cause of defects involves scanning of a semiconductor wafer with an optical wafer inspection tool. The optical wafer inspection tool provides information on position and equivalent sizes of defects. The information obtained from traditional optical wafer inspection tools is often insufficient to identify the root cause of defects. Semiconductor wafers are then scanned in electron based wafer review systems to determine the shape of defects. Electron based wafer review systems are extremely slow. In order to speed up the process of determining the shape of defects, information on position of defects obtained from optical wafer inspection tools is fed into electron based wafer review tools.

Traditional wafer inspection suffers from a number of problems: a) need for multiple systems to identify root-cause of defects, b) increased down time in fabrication, c) complex position matching requirement between multiple systems, and d) electron based review systems use high energy electron beams that could damage intricate structures on wafer.

Accordingly, there is a need for improved wafer inspection that eliminates the need for multiple systems to identify root-cause of defects, minimizes down time in fabrication, eliminates the need for complex position matching requirement between multiple systems, and eliminates use of high energy electron beams that could damage intricate structures on wafer.

SUMMARY

The invention is a method for designing a filter to image a feature on a surface. Further, the invention is also a system and method for recognizing a feature on a surface.

In some embodiments, the invention is a method for designing a filter to image a feature on a surface, comprising: acquiring an image of said feature, with said image of feature comprising information from multiple points of said feature; generating a structural model of said feature by extracting predetermined properties of said feature from said image of feature; computing a scattering model for said feature from said structural model of said feature, with said scattering model for feature having information on scattered electromagnetic field from feature propagating in a plurality of scattering angles, wherein said scattered electromagnetic field from feature is generated by scattering of an electromagnetic radiation by said feature; acquiring an image of said surface, with said image of surface comprising information from multiple points of said surface; generating a structural model of said surface by extracting predetermined properties of said surface from said image of surface; computing a scattering model for said surface from said structural model of said surface, with said scattering model for surface having information on scattered electromagnetic field from surface propagating in a plurality of scattering angles, wherein said scattered electromagnetic field from surface is generated by scattering of an electromagnetic radiation by said surface; and computing said filter by combining said scattering model for feature and said scattering model for surface to achieve a predetermined filter performance metric, whereby said filter is designed to modulate scattered electromagnetic field from said feature and scattered electromagnetic field from said surface to image a feature on said surface.

In some embodiments, the invention is a method for recognizing a feature, comprising: acquiring an image of said feature using an imaging module, with said image of feature comprising information from multiple points of said feature; computing a feature spread function from scattering model of a previously known feature and transfer function of said imaging module, wherein said feature spread function represents a model of an image of said previously known feature; and comparing said image of feature with said feature spread function by computing a match metric between said image of feature and said feature spread function, whereby said match metric determines if said feature is similar to said previously known feature.

In some embodiments, the invention is a system for recognizing a feature, comprising: an imaging module focusing electromagnetic radiation scattered by said feature; an image sensor capturing said radiation to generate an image of said feature, with said image of feature comprising information from multiple points of said feature; and a processor configured to compute a feature spread function from scattering model of a previously known feature and transfer function of said imaging module, wherein said feature spread function represents a model of an image of said previously known feature; compare said image of feature with said feature spread function by computing a match metric of said image of feature and said feature spread function, whereby said match metric determines if said feature is similar to said previously known feature.

DETAILED DESCRIPTION OF THE PREFERRED EMBODIMENTS

Figure 1:
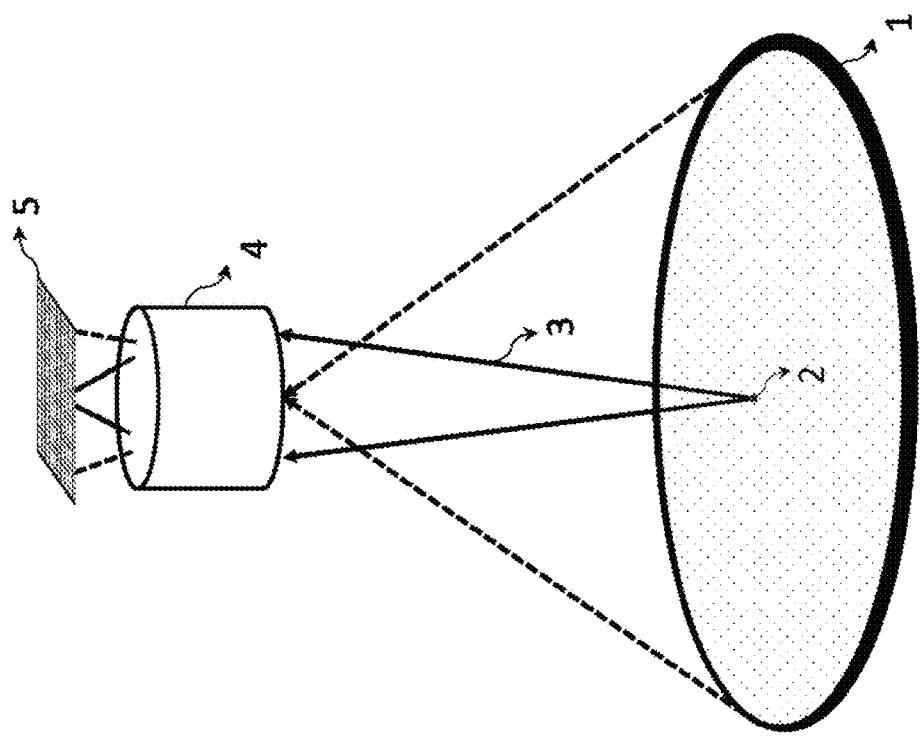
FIG. 1 shows an imaging module collecting scattered radiation from a wide area of a surface and focusing the radiation on an image sensor, in accordance with the invention.

FIG. 1 shows an imaging module 4 collecting scattered radiation from a wide area of a surface 1 and focusing the radiation on an image sensor 5, in accordance with the invention. A feature 2 present on surface 1 scatters electromagnetic radiation incident on it. In some embodiments, surface 1 is a semiconductor wafer. Features include abnormalities or defects and other structures present on surface 1. Abnormalities or defects include particles, process induced defects, crystal originated pits, residues, scratches, and bumps. The scattered radiation 3 from feature 2 is collected by imaging module 4. The scattered radiation 3 is an electromagnetic field generated by feature 2. Accordingly, the intensity and phase of scattered radiation 4 is dependent on the properties of feature 2. Imaging module 4 collects scattered radiation 3. In some embodiments, imaging module 4 comprises a filter to modulate electromagnetic radiation to enhance imaging performance. The field of view of imaging module 4 covers a substantial area of surface 1. Accordingly, features from a wide area of surface 1 are detected by image sensor 5. In some embodiments, image sensor 5 is a complementary metal oxide semiconductor type imager. In other embodiments, image sensor 5 is a charge coupled device type imager. The image sensor 5 comprises a plurality of photodetectors called pixels. Imaging module 4 comprises zoom and focus controls. Zoom control is used to control the field of view of imaging module. Focus control is used to generate a focused or a defocused image of surface 1.

Figure 2:
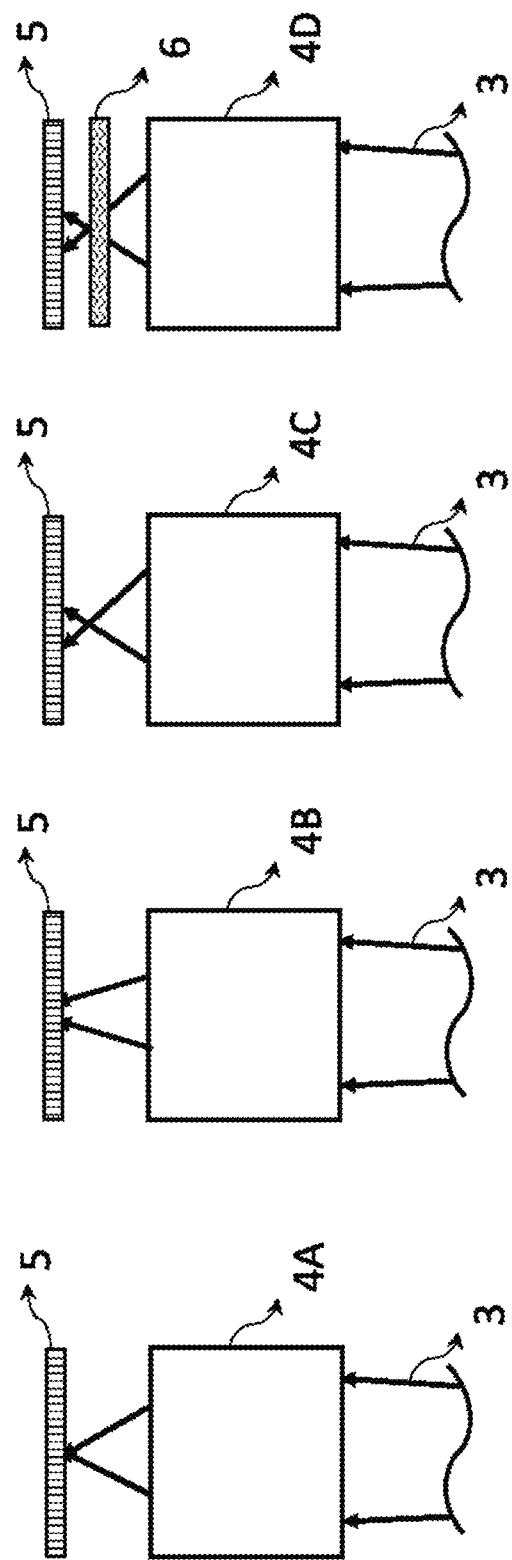
FIG. 2A depicts an imaging module focusing radiation on the plane of an image sensor, in accordance with the invention.
FIG. 2B depicts an image sensor detecting defocused radiation from an imaging module, with the focal plane of the imaging module located behind the image sensor, in accordance with the invention.
FIG. 2C depicts an image sensor detecting defocused radiation from an imaging module, with the focal plane of the imaging module located in front of the image sensor, in accordance with the invention.
FIG. 2D depicts an imaging module focusing radiation on a micro-optic sensor layer, and an image sensor detecting radiation from the micro-optic sensor layer, in accordance with the invention.

FIG. 2A depicts an imaging module 4A focusing radiation on the plane of an image sensor 5, in accordance with the invention. Scattered radiation 3 from a feature is incident on imaging module 4A. In some embodiments, imaging module is tuned to focus scattered radiation 3 on image sensor 5. In other embodiments, the distance between image sensor 5 and imaging module 4A is tuned to focus scattered radiation 3 on image sensor 5. A focused image maximizes intensity of image pixels of sensor 5. In some embodiments, focused images are used for precisely estimating the position of intensity peaks imaged on the sensor 5. Information about the position of intensity peaks is transformed into position of features on a surface by multiplying the position of intensity peaks with the magnification of imaging module.

FIG. 2B depicts an image sensor 5 detecting defocused radiation from an imaging module 4B, with the focal plane of the imaging module located behind the image sensor, in accordance with the invention. Scattered radiation 3 from a feature is incident on imaging module 4B. In some embodiments, the imaging module is tuned so that the focal plane of scattered radiation lies behind image sensor 5. In other embodiments, the distance between image sensor 5 and imaging module 4B is tuned so that the focal plane of scattered radiation lies behind image sensor 5. Accordingly, image sensor 5 detects a defocused image of scattered radiation. The defocused scattered radiation is detected by more number of pixels in a defocused image when compared to the number of pixels spanned by a focused scattered radiation in a focused image. Defocused images are useful to recognize shapes of features due to the detection of scattered radiation by more number of pixels.

FIG. 2C depicts an image sensor 5 detecting defocused radiation from an imaging module 4C, with the focal plane of the imaging module located in front of the image sensor, in accordance with the invention. Scattered radiation 3 from a feature is incident on imaging module 4C. In some embodiments, the imaging module is tuned so that the focal plane of scattered radiation lies in front of image sensor 5. In other embodiments, the distance between image sensor 5 and imaging module 4C is tuned so that the focal plane of scattered radiation lies in front of image sensor 5. Accordingly, image sensor 5 detects a defocused image of scattered radiation. The defocused scattered radiation is detected by more number of pixels in a defocused image when compared to the number of pixels spanned by a focused scattered radiation in a focused image. Defocused images are useful to recognize shapes of features due to the detection of scattered radiation by more number of pixels.

FIG. 2D depicts an imaging module 4D focusing radiation on a micro-optic sensor layer 6, and an image sensor 5 detecting radiation from the micro-optic sensor layer 6, in accordance with the invention. Scattered radiation 3 from a feature is incident on imaging module 4D. The micro-optic sensor layer is used for detecting phase of scattered radiation. The micro-optic sensor layer 6 comprises a plurality of lenses implemented as a refractive optical element or a diffractive optical element. In some embodiments, each lens of the micro-optic sensor layer generates an image of the aperture of the imaging optic 4D on the pixels of image sensor 5. A finite number of pixels are allocated in image sensor 5 for each lens on the micro-optic sensor layer 6. The pixels allocated for a lens of micro-optic sensor layer 6 are located around the center of the optical axis of the lens. From the intensities of pixels allocated for the lens, the phase gradient of scattered radiation incident on the lens is determined. For example, if the pixel intensity corresponds to a focused spot in the center of the allocated pixels (on the optical axis of lens), then the scattered radiation can be estimated to have a zero phase gradient when it is incident on the surface of the lens. Alternatively, if the pixel intensity corresponds to a focused spot that is not at the center of the allocated pixels for the lens, then the scattered light can be estimated to have a linear phase gradient that is proportional to the distance between the focused spot and the center of allocated pixels. Accordingly, a phase gradient value can be estimated for each lens of the micro-optic sensor layer 6. A phase gradient profile for the surface of the micro-optic sensor layer 6 can be estimated by combining phase gradients of a plurality of lenses in the micro-optic sensor layer 6 using a stitching algorithm. The phase profile of scattered radiation, P(x,y), is computed from the estimated phase gradient profile by calculating a two dimensional integration of the phase gradient profile. The intensity of scattered light, I(x,y), is obtained from the pixel intensities detected by image sensor 5. The electromagnetic field of scattered light, C(x,y), is calculated from the intensity and phase of scattered radiation as, $C(x,y)=\sqrt{I(x,y)}e^{(-iP(x,y))}$. The electromagnetic field C(x,y) may then be propagated using computational propagation to bring different planes in focus. For example, C(x,y) may be computationally propagated to bring a surface in focus. Alternatively, C(x,y) may be propagated to bring a plane above or below a surface in focus, thereby generating a defocused image of a surface.

In some embodiments, computational propagation is performed in the spatial frequency domain by first computing spatial frequencies of electromagnetic field using a transformation. Then, a propagation transfer function is computed and multiplied with spatial frequencies of the electromagnetic field. In some embodiments, computing spatial frequencies of an electromagnetic field involves the calculation of $\tilde{C}(k_x,k_y)=F\{C(x,y)\}$, where C(x,y) is electromagnetic field, F refers to Fourier transform, and $\tilde{C}(k_x,k_y)$ is the spatial frequency of C(x,y). Propagation transfer function, $\tilde{H}(k_x,k_y)$, is computed as, $$\tilde{H}(k_x, k_y) = e^{\left(i\Delta z\sqrt{(k^2-k_x^2-k_y^2)}\right)},$$

where $k=2\pi n/\lambda$, n is a redrfractive index, $\lambda$, is the wavelength of the electromagnetic beam, and $\Delta z$ is the distance through which the electromagnetic field is propagated. The electromagnetic field after propagation is computed as, $F^{-1}\{\tilde{C}(k_x,k_y)\tilde{H}(k_x,k_y)\}$, where $F^{-1}$ refers to inverse Fourier transformation. In other embodiments, computational propagation of an electromagnetic field is performed by first computing an impulse response or point spread function of propagation, and then computing a convolution of the electromagnetic field with the impulse response. The impulse response of propagation is calculated as $$F^{-1}\left\{e^{\left(i\Delta z\sqrt{(k^2-k_x^2-k_y^2)}\right)}\right\}.$$

In some embodiments, $\Delta z$ is calculated as the product of the square of the magnification of imaging module 4D with the distance in z through which the field needs to be propagated in the object space of imaging module 4D. In some embodiments, computational propagation may be achieved by using digital refocusing algorithms that operate in the geometrical optics regime by rearranging pixel values to compute different focal planes.

Figure 3:
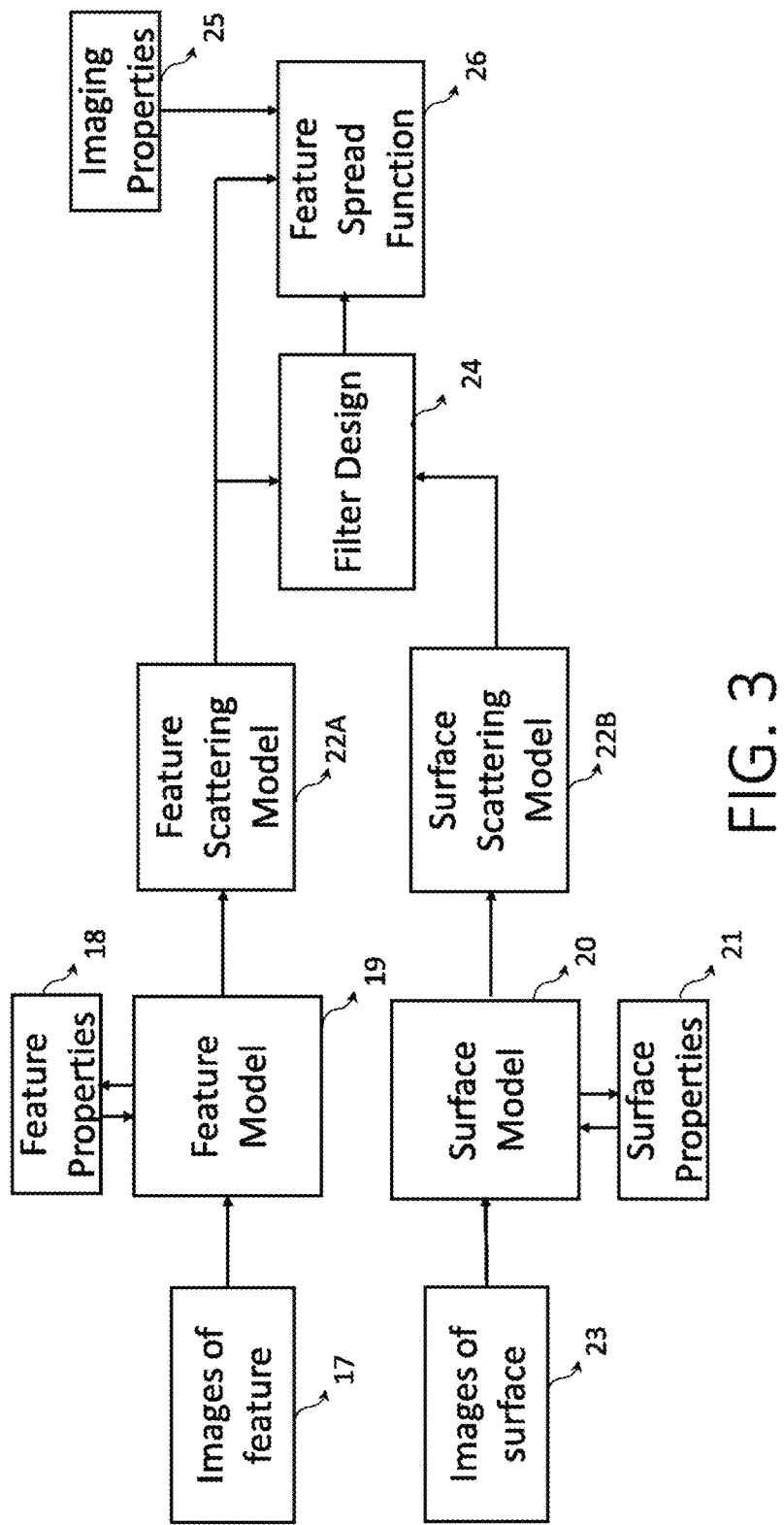
FIG. 3 illustrates a block diagram for designing a filter and designing a feature spread function based on computing light scattering models for feature and surface, in accordance with the invention.

FIG. 3 illustrates a block diagram for designing a filter and designing a feature spread function based on computing light scattering models for feature and surface, in accordance with the invention. The filter is designed to modulate scattered electromagnetic field from feature and scattered electromagnetic field from surface to image the feature on said surface. In block 17, images of feature are acquired. Each image of feature comprises information from multiple points of the feature. The images may be captured using a variety of techniques including scanning electron microscope, atomic force microscope, near field optical microscope, and optical microscope. In some embodiments, images may be captured with multiple illumination angles. In other embodiments, images may be captures with multiple views. In block 19, a structural model for feature is generated by extracting predetermined properties from acquired images of feature. The structural model may be a two dimensional or a three dimensional model of the feature. The structural model of feature describes the shape of the feature. In some embodiments, the shape of the feature is determined from the brightness of pixels in images of feature. In some embodiments, two dimensional shape may be obtained by using image segmentation to separate feature pixels from background pixels. In some embodiments, the third dimension of feature is extracted from images acquired with multiple illumination angles. For example, a photometric stereo algorithm may be used to extract the third dimension. In some embodiments, a structural model of feature is generated by extracting a shape gradient from brightness of multiple points in image of feature. In other embodiments, the third dimension of feature is extracted from images acquired with multiple views. For example, a stereo matching algorithm may be employed to estimate the relative displacement of a feature point in multiple views. The displacement thus estimated is transformed into the third dimension using camera parameters such as focal length and baseline. The structural model of feature thus estimated has quantitative dimensions. In some embodiments, each point on the structural model has a three dimensional position coordinate associated with it. In other embodiments, each point on the structural model has a two dimensional position coordinate associated with it. In addition to information on shape of the feature, the structural model also comprises information on material composition of the feature. This includes information on permittivity and permeability of the material of feature. Block 18 comprises properties corresponding to a number of features. Properties include permittivity and permeability of a variety of materials. In some embodiments, a mapping between shape and material properties is used. In other words, material properties are loaded from the shape of feature. In some embodiments, block 19 provides a structural model to block 18, and block 18 provides material properties based on the structural model received from block 19. In other embodiments, block 19 classifies a structural model into one of many feature types, and provides the feature type information to block 18. In such embodiments, block 18 provides material properties based on feature type information received from block 18. In some embodiments, feature type is provided to block 19 along with images of feature 17. In other embodiments, material properties are provided to block 19 along with images of feature 17. Feature type may be determined from a given structural model by comparing the structural model with structural models of previously known feature types. In block 22A, a scattering model is computed from the structural model of feature. Information on wavelength, polarization, and an angle of incidence of an electromagnetic beam is made available to block 22A. Scattering model comprises information on scattered radiation in a plurality of polar and azimuthal angles. The scattered radiation is generated by scattering of the electromagnetic radiation by the feature. Information on scattered radiation includes intensity, phase, polarization, and wavelength of scattered radiation. In some embodiments, the structural model of feature is placed over a smooth surface so as to take the effects of interaction between feature and surface into account while calculating the scattering model. In other embodiments, the structural model of feature is located in a homogeneous medium while calculating the scattering model. In such embodiments, scattering in forward scattering angles are flipped by the angle between electromagnetic beam and the plane of surface so that forward scattering angles are centered on specular reflection of beam. Such a flipping of forward scattered radiation accounts for reflection of scattering in forward scattering angles by the surface. For simple shapes of structural model, such as a sphere, scattering model may be computed using analytical models. In some embodiments, Mie scattering may be used to calculate the scattering model if the structural model of feature is substantially similar to a sphere. In other embodiments, T-Matrix scattering method may be used to calculate the scattering model if the structural model of feature is substantially rotationally symmetric. Rotationally symmetric features include spheres, prolate spheroids, and oblate spheroids. In some embodiments, a finite element method may be used to calculate the scattering model if the structural model of feature is not symmetric. In other embodiments, a finite difference time domain method may be used to calculate the scattering model if the structural model of feature is not symmetric. In some embodiments, scattering model is computed by discretizing the structural model into a plurality of points located on a grid; computing electric field and magnetic field values at the points; and propagating the electric field using a near-to-far field transformation. In some embodiments, the near-to-far field transformation is computed using a Fourier Transform operation. In some embodiments, discrete dipole approximation is used to calculate the scattering model if the structural model of feature is not symmetric. In some embodiments, Rayleigh scattering is used to calculate the scattering model if the size of the structural model of feature is much smaller than the wavelength of electromagnetic radiation. In some embodiments, separation of variables method is used to calculate the scattering model if the structural model of feature substantially is similar to a spheroid. In some embodiments, point matching method is used to calculate the scattering model of feature. In some embodiments, integral equation methods such as method of moments is used to calculate the scattering model of feature. In some embodiments, Fredholm integral equation method is used to calculate the scattering model of feature. In some embodiments, superposition method is used to calculate the scattering model if the structural model of feature is substantially similar to a compounded spheroid or a compounded sphere. In some embodiments, geometric optics is used to calculate the scattering model if the size of the structural model of feature is much larger than the wavelength of electromagnetic radiation. In some embodiments, Rayleigh-Gans scattering is used to calculate the scattering model of the feature. In some embodiments, Fresnel or Fraunhofer diffraction is used to calculate the scattering model of the feature.

In block 23, images of surface are acquired. The images may be captured using a variety of techniques including scanning electron microscope, atomic force microscope, near field optical microscope, and optical microscope. In some embodiments, images may be captured with multiple illumination angles. In other embodiments, images may be captures with multiple views. In block 20, a structural model for surface is generated by extracting predetermined properties from acquired images of surface. The structural model is a three dimensional model of the surface. The surface model describes the quantitative shape of the surface. In some embodiments, the shape of the surface is determined from the brightness of pixels in images of surface. The structural model of surface thus estimated has quantitative dimensions. In some embodiments, each point on the structural model has a three dimensional position coordinate associated with it. In addition to information on shape of the surface, the structural model also has information on material composition of the surface. This includes information on permittivity and permeability of the material of surface. Block 21 comprises material properties of a number of surfaces. Properties include permittivity and permeability of a variety of materials. In some embodiments, a mapping between shape and material properties is available in block 21. In other words, material properties are loaded from the shape of surface. In some embodiments, block 20 provides a structural model of surface to block 21, and block 21 provides material properties based on the structural model received from block 20. In other embodiments, block 20 classifies a structural model into one of many surface types, and provides the surface type information to block 21. In such embodiments, block 21, provides material properties based on surface type information received from block 20. In some embodiments, surface type is provided to block 20 along with images of surface 23. In other embodiments, material properties are provided to block 20 along with images of surface 23. Surface type may be determined from a given structural model by comparing the structural model with structural models of previously known surface types. In block 22B, a scattering model is computed from the structural model of surface. Information on wavelength, polarization, and an angle of incidence of an electromagnetic beam is made available to block 22B. Scattering model comprises information on scattered radiation in a plurality of polar and azimuthal angles. The scattered radiation is generated by scattering of an electromagnetic radiation by the surface. Information on scattered radiation includes intensity, phase, polarization, and wavelength of scattered radiation. In some embodiments, a finite element method may be used to calculate the scattering model of surface. In other embodiments, a finite difference time domain method may be used to calculate the scattering model of surface. In some embodiments, scattering model is computed by discretizing the structural model into a plurality of points located on a grid; computing electric field and magnetic field values at the points; and propagating the electric field using a near-to-far field transformation. In some embodiments, the near-to-far field transformation is computed using a Fourier Transform operation. In some embodiments, discrete dipole approximation is used to calculate the scattering model of surface. In some embodiments, Fresnel or Fraunhofer diffraction is used to calculate the scattering model of the surface. In some embodiments, a bidirectional reflection distribution function is used to calculate the scattering model of surface. In some embodiments, an ensemble roughness metric for surface height deviation (relative to an average surface height value), such as a root mean square deviation, is computed. Further, an autocorrelation of surface profile is computed. A correlation length, a parameter quantifying the width of the autocorrelation plot, is estimated. A total integrated scatter is calculated from the ensemble roughness metric, correlation length, angle of incidence of electromagnetic beam, and wavelength of electromagnetic radiation. A power spectral density function is computed as the Fourier transform of the autocorrelation of surface profile. In some embodiments, the scattering of surface is modeled from the power spectral density function of surface profile. In some embodiments, the scattering of surface modeled from the power spectral density function is normalized so that the integral of power spectral density function is equal to total integrated scatter. In some embodiments, the scattering of surface is modeled by transforming the structural model of surface to the frequency domain. In some embodiments, the scattering of surface is modeled by computing a Fourier Transformation of the structural model of surface. The scattering model of surface thus computed may be normalized such that the integral of scattering model is equal to the total integrated scatter.

In block 24, a filter is designed based on the scattering model of feature and scattering model of surface to achieve a predetermined filter performance metric. It is generally desired that scattered radiation from feature is maximized and scattered radiation from surface is minimized after filtering so as to maximize feature sensitivity. Consider $F(\theta,\varphi)$ to be the scattering model of feature, where $\theta$ is the polar angle and $\varphi$ is the azimuthal angle. Similarly, consider $S(\theta,\varphi)$ to be the scattering model of surface. Both F and S are complex electromagnetic fields having an intensity and phase value at each $\theta$ and $\varphi$. Filter $H(\theta,\varphi)$ is calculated from $F(\theta,\varphi)$ and $S(\theta,\varphi)$. In some embodiments, $H(\theta,\varphi)$ is directly proportional to $F(\theta,\varphi)$. In some embodiments, $H(\theta,\varphi)$ is directly proportional to $F^*(\theta,\varphi)$, where $F^*(\theta,\varphi)$ is the complex conjugate of $F(\theta,\varphi)$. In some embodiments, $H(\theta,\varphi)$ is inversely proportional to $S(\theta,\varphi)$. In some embodiments, the predetermined performance metric comprises maximizing the ratio of scattered power from feature to scattered power from surface. In some embodiments, $H(\theta,\varphi)$ is directly proportional to $F(\theta,\varphi)$ and inversely proportional to $S(\theta,\varphi)$. In some embodiments, the filter is designed by computing the ratio of intensity of scattered electromagnetic field of feature to intensity of scattered electromagnetic field of surface. In some embodiments, the filter is designed by computing a matched filter of said scattered electromagnetic field of feature. In some embodiments, $H(\theta,\varphi)$ is directly proportional to $F^*(\theta,\varphi)$, and inversely proportional to $S(\theta,\varphi)$.

In block 25, a feature spread function FSF(m,n) is calculated from scattering model of feature $F(\theta,\varphi)$, scattering model of a surface $S(\theta,\varphi)$, filter function $H(\theta,\varphi)$, and from imaging properties of an imaging module $A(\theta,\varphi)$. Block 25 provides information on imaging properties of the imaging module. $A(\theta,\varphi)$ comprises information on the range of scattering angles collected by the imaging module. In addition, $A(\theta,\varphi)$ comprises information on the optical aberrations of imaging module. Aberrations include shift, defocus, coma, spherical, and astigmatism. For example, when the imaging module is focused in front of an image sensor, a positive defocus is introduced in $A(\theta,\varphi)$. And when the imaging module is focused behind an image sensor, a negative defocus is introduced in $A(\theta,\varphi)$. When the imaging module is focused on the plane of an image sensor, no defocus is introduced in $A(\theta,\varphi)$. In some embodiments, $A(\theta,\varphi)$ is space invariant. That is, $A(\theta,\varphi)$ does not vary with position on image sensor. In other embodiments, $A(\theta,\varphi)$ is space variant. That is, $A(\theta,\varphi)$ varies with position on image sensor. In some embodiments computational propagation is performed to compute an image of surface. In these embodiments, parameters of computational propagation are also incorporated in $A(\theta,\varphi)$. For example, the distance through which the complex field is propagated is incorporated along with the defocus parameter of $A(\theta,\varphi)$. The net properties of imaging module is represented by the transfer function of imaging module, $T(\theta,\varphi)$, which is calculated as $T(\theta,\varphi)=H(\theta,\varphi)*A(\theta,\varphi)$. In some embodiments, feature spread function is computed by transforming the product of $F(\theta,\varphi)$ and $T(\theta,\varphi)$ from spatial frequency domain to image domain. In some embodiments, computing a feature spread function comprises multiplying the scattering model of a previously known feature with the transfer function of imaging module to generate a feature transfer function, and transforming said feature transfer function from spatial frequency domain to image domain. In some embodiments, feature spread function is computed as $FSF(m,n)=|FT^{-1}\{F(\theta,\varphi)*T(\theta,\varphi)\}|^2$, where $FT^{-1}$ refers to inverse Fourier transformation. In some embodiments, computing a feature spread function comprises transforming the scattering model from spatial frequency domain to image domain for generating a feature response, and convolving the feature response with point spread function of said imaging module. In some embodiments, the point spread function of imaging module is computed as $|FT^{-1}\{T(\theta,\varphi)\}|^2$. In some embodiments, the feature response is computed as $|FT^{-1}\{F(\theta,\varphi)\}|^2$.

Figure 4:
FIG. 4 shows an exemplary flow chart describing steps for computing a filter from scattering models for feature and surface, in accordance with the invention.

FIG. 4 shows an exemplary flow chart describing steps for computing a filter from scattering models for feature and surface, in accordance with the invention. In block 32, images of feature are acquired. Each image of feature comprises information from multiple points of the feature. The images may be captured using a variety of techniques including scanning electron microscope, atomic force microscope, near field optical microscope, and optical microscope. In some embodiments, images may be captured with multiple illumination angles. In other embodiments, images may be captures with multiple views. In block 33, a structural model for feature is generated by extracting predetermined properties from acquired images of feature. The structural model may be a two dimensional or a three dimensional model of the feature. The structural model describes the shape of the feature. In some embodiments, the shape of the feature is determined from the brightness of pixels in images of feature. In some embodiments, two dimensional shape may be obtained by using image segmentation to separate feature pixels from background pixels. In some embodiments, the third dimension of feature is extracted from images acquired with multiple illumination angles. For example, a photometric stereo algorithm may be used to extract the third dimension. In some embodiments, generating a structural model of feature comprises extracting a shape gradient from brightness of multiple points in image of feature. In other embodiments, the third dimension of feature is extracted from images acquired with multiple views. For example, a stereo matching algorithm may be employed to estimate the relative displacement of a feature point in multiple views. The displacement thus estimated is transformed into the third dimension using camera parameters such as focal length and baseline. The structural model of feature thus estimated has quantitative dimensions. In some embodiments, each point on the structural model has a three dimensional position coordinate associated with it. In other embodiments, each point on the structural model has a two dimensional position coordinate associated with it. In addition to information on shape of the feature, the structural model also has information on material composition of the feature. This includes information on permittivity and permeability of the material of feature. Block 33 comprises properties of a variety of features. Properties include permittivity and permeability of a variety of materials. In some embodiments, a mapping between shape and material properties is made available. In other words, material properties are loaded from the shape of feature. In some embodiments, feature type is provided to block 33 along with images of feature. In other embodiments, material properties are provided to block 33 along with images of feature. Feature type may be determined from a given structural model by comparing the structural model with structural models of previously known feature types. In block 34, a scattering model is computed from the structural model of feature. Information on wavelength, polarization, and an angle of incidence of an electromagnetic beam is made available to block 34. Scattering model comprises information on scattered radiation in a plurality of polar and azimuthal angles. The scattered radiation is generated by scattering of an electromagnetic radiation by the feature. Information on scattered radiation includes intensity, phase, polarization, and wavelength of scattered radiation. In some embodiments, the structural model of feature is placed over a smooth surface so as to take the effects of interaction between feature and surface into account while calculating the scattering model. In other embodiments, the structural model of feature is located in a homogeneous medium while calculating the scattering model. In such embodiments, scattering in forward scattering angles are flipped by the angle between electromagnetic beam and the plane of surface so that forward scattering angles are centered on specular reflection of beam. Such a flipping of forward scattered radiation accounts for reflection of scattering in forward scattering angles by the surface. For simple shapes of structural model, such as a sphere, scattering model may be computed using analytical models. In some embodiments, Mie scattering may be used to calculate the scattering model if the structural model of feature is substantially similar to a sphere. In other embodiments, T-Matrix scattering method may be used to calculate the scattering model if the structural model of feature is substantially rotationally symmetric. Rotationally symmetric features include spheres, prolate spheroids, and oblate spheroids. In some embodiments, a finite element method may be used to calculate the scattering model if the structural model of feature is not symmetric. In other embodiments, a finite difference time domain method may be used to calculate the scattering model if the structural model of feature is not symmetric. In some embodiments, scattering model is computed by discretizing the structural model into a plurality of points located on a grid; computing electric field and magnetic field values at the points; and propagating the electric field using a near-to-far field transformation. In some embodiments, the near-to-far field transformation is computed using a Fourier Transform operation. In some embodiments, discrete dipole approximation is used to calculate the scattering model if the structural model of feature is not symmetric. In some embodiments, Rayleigh scattering is used to calculate the scattering model if the size of the structural model of feature is much smaller than the wavelength of electromagnetic radiation. In some embodiments, separation of variables method is used to calculate the scattering model if the structural model of feature substantially is similar to a spheroid. In some embodiments, point matching method is used to calculate the scattering model of feature. In some embodiments, integral equation methods such as method of moments is used to calculate the scattering model of feature. In some embodiments, Fredholm integral equation method is used to calculate the scattering model of feature. In some embodiments, superposition method is used to calculate the scattering model if the structural model of feature substantially is similar to a compounded spheroid or a compounded sphere. In some embodiments, geometric optics is used to calculate the scattering model if the size of the structural model of feature is much larger than the wavelength of electromagnetic radiation. In some embodiments, Rayleigh-Gans scattering is used to calculate the scattering model of the feature. In some embodiments, Fresnel or Fraunhofer diffraction is used to calculate the scattering model of the feature.

In block 35, images of surface are acquired. The images may be captured using a variety of techniques including scanning electron microscope, atomic force microscope, near field optical microscope, and optical microscope. In some embodiments, images may be captured with multiple illumination angles. In other embodiments, images may be captures with multiple views. In block 36, a structural model for surface is generated by extracting predetermined properties from acquired images of surface. The structural model is a three dimensional model of the surface. The surface model describes the shape of the surface. In some embodiments, the shape of the surface is determined from the brightness of pixels in images of surface. The structural model of surface thus estimated has quantitative dimensions. In some embodiments, each point on the structural model has a three dimensional position coordinate associated with it. In addition to information on shape of the surface, the structural model also has information on material composition of the surface. This includes information on permittivity and permeability of the material of surface. Block 36 comprises properties of a variety of surfaces. Properties include permittivity and permeability of a variety of materials. In some embodiments, a mapping between shape and material properties is available in block 36. In other words, material properties are loaded from the shape of surface. In some embodiments, surface type is provided to block 36 along with images of surface. In other embodiments, material properties are provided to block 36 along with images of surface. Surface type may be determined from a given structural model by comparing the structural model with structural models of previously known surface types. In block 37, a scattering model is computed from the structural model of surface. Information on wavelength, polarization, and an angle of incidence of an electromagnetic beam is made available to block 37. Scattering model comprises information on scattered radiation in a plurality of polar and azimuthal angles. The scattered radiation is generated by scattering of an electromagnetic radiation by the surface. Information on scattered radiation includes intensity, phase, polarization, and wavelength of scattered radiation. In some embodiments, a finite element method may be used to calculate the scattering model of surface. In other embodiments, a finite difference time domain method may be used to calculate the scattering model of surface. In some embodiments, scattering model is computed by discretizing the structural model into a plurality of points located on a grid; computing electric field and magnetic field values at the points; and propagating the electric field using a near-to-far field transformation. In some embodiments, the near-to-far field transformation is computed using a Fourier Transform operation. In some embodiments, discrete dipole approximation is used to calculate the scattering model of surface. In some embodiments, Fresnel or Fraunhofer diffraction is used to calculate the scattering model of the surface. In some embodiments, a bidirectional reflection distribution function is used to calculate the scattering model of surface. In some embodiments, an ensemble roughness metric for surface height deviation (relative to an average surface height value), such as a root mean square deviation, is computed. Further, an autocorrelation of surface profile is computed. A correlation length, a parameter quantifying the width of the autocorrelation plot, is estimated. A total integrated scatter is calculated from the ensemble roughness metric, correlation length, angle of incidence of electromagnetic beam, and wavelength of electromagnetic radiation. A power spectral density function is computed as the Fourier transform of the autocorrelation of surface profile. In some embodiments, the scattering of surface is modeled from the power spectral density function of surface profile. In some embodiments, the scattering of surface modeled from the power spectral density function is normalized so that the integral of power spectral density function is equal to total integrated scatter. In some embodiments, the scattering of surface is modeled by transforming the structural model of surface to the frequency domain. In some embodiments, the scattering of surface is modeled by computing a Fourier Transformation of the structural model of surface. The scattering model of surface thus computed may be normalized such that the integral of scattering model is equal to the total integrated scatter.

In block 38, a filter is designed based on scattering model of feature and scattering model of surface to achieve a predetermined filter performance metric. It is generally desired that scattered radiation from feature is maximized and scattered radiation from surface is minimized after filtering so as to maximize feature sensitivity. Consider $F(\theta,\varphi)$ to be the scattering model of feature, where $\theta$ is the polar angle and $\varphi$ is the azimuthal angle. Similarly, consider $S(\theta,\varphi)$ to be the scattering model of surface. Both F and S are complex electromagnetic fields having an intensity and phase value at each $\theta$ and $\varphi$. Filter $H(\theta,\varphi)$ is calculated from $F(\theta,\varphi)$ and $S(\theta,\varphi)$. In some embodiments, $H(\theta,\varphi)$ is directly proportional to $F(\theta,\varphi)$. In some embodiments, $H(\theta,\varphi)$ is directly proportional to $F^*(\theta,\varphi)$, where $F^*(\theta,\varphi)$ is the complex conjugate of $F(\theta,\varphi)$. In some embodiments, $H(\theta,\varphi)$ is inversely proportional to $S(\theta,\varphi)$. In some embodiments, the predetermined performance metric comprises maximizing the ratio of scattered power from feature to scattered power from surface. In some embodiments, $H(\theta,\varphi)$ is directly proportional to $F(\theta,\varphi)$ and inversely proportional to $S(\theta,\varphi)$. In some embodiments, the filter is designed by computing the ratio of intensity of scattered electromagnetic field of feature to intensity of scattered electromagnetic field of surface. In some embodiments, the filter is designed by computing a matched filter of said scattered electromagnetic field of feature. In some embodiments, $H(\theta,\varphi)$ is directly proportional to $F^*(\theta,\varphi)$, and inversely proportional to $S(\theta,\varphi)$.

Figure 5:
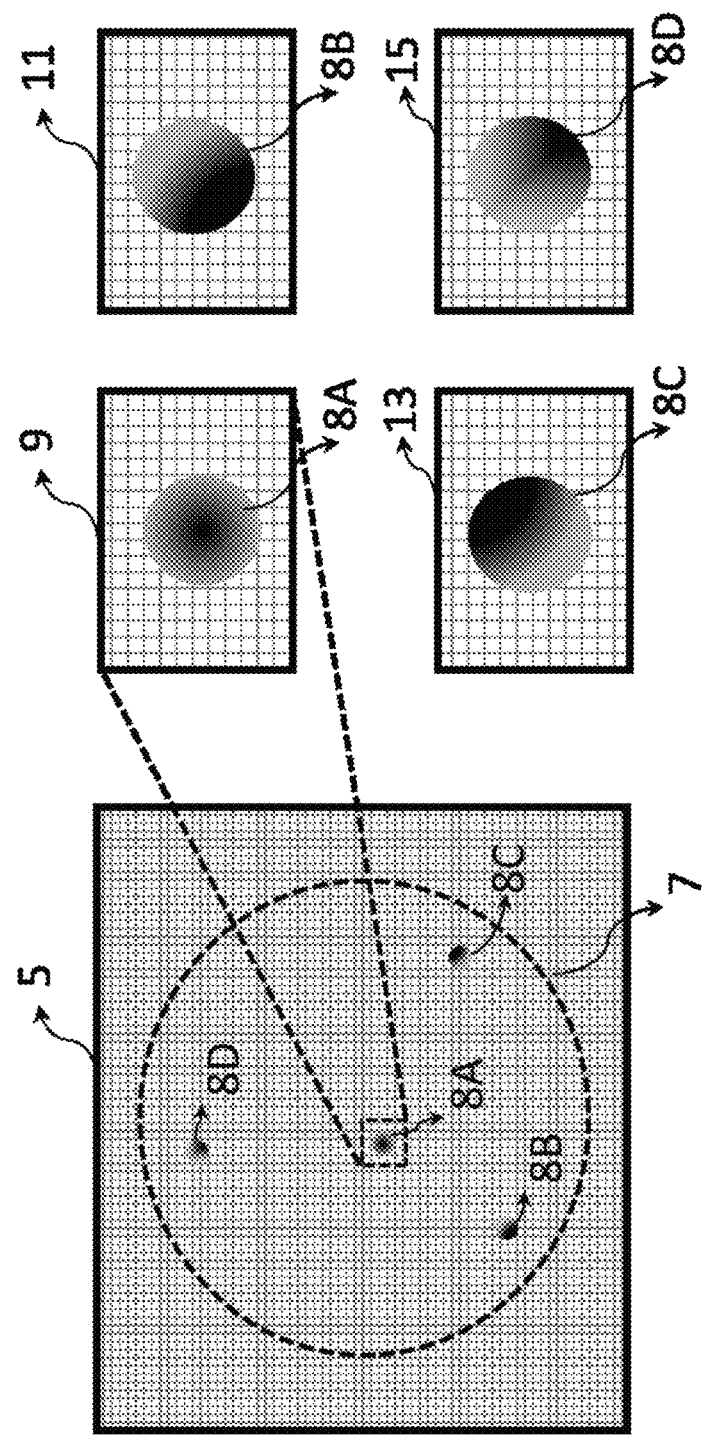
FIG. 5 illustrates an image comprising multiple features, in accordance with the invention.

FIG. 5 illustrates an image comprising multiple features, in accordance with the invention. An image 5 captured by an image sensor captures scattered radiation from a surface. An image of multiple features of the surface is captured within a region 7 bounded by the contour of surface. Four feature pixel regions, 8A, 8B, 8C, and 8D, corresponding to four features are detected in image 5. A close up of feature pixel region 8A is shown in pixel region 9. Similarly, a close up of feature pixel region 8B is shown in pixel region 11. A close up of feature pixel region 8C is shown in pixel region 13. Finally, a close up of feature pixel region 8D is shown in pixel region 5. The shapes of the four feature pixel regions are seen to be different from each other. The difference in shape between the feature pixel regions is primarily due to the difference in the scattering profiles of the features generating the feature pixel regions. The difference in scattering profiles of features is due to different shapes and material properties of the features. When the imaging module is spatially variant, the differences in the shapes of feature pixel region could also be because of the positions of the feature pixel regions on the image sensor. In embodiments where the image sensor comprises a micro-optic sensor layer, image 5 represents the image after reconstruction of an image from raw image detected by the image sensor. In some embodiments, reconstruction of raw image involves computation of intensity and phase of detected scattered radiation and computational propagation of scattered radiation to a desired axial plane. In some embodiments, the image is focused on the surface. In other embodiments, the image is focused above or below the plane of surface.

Figure 6:
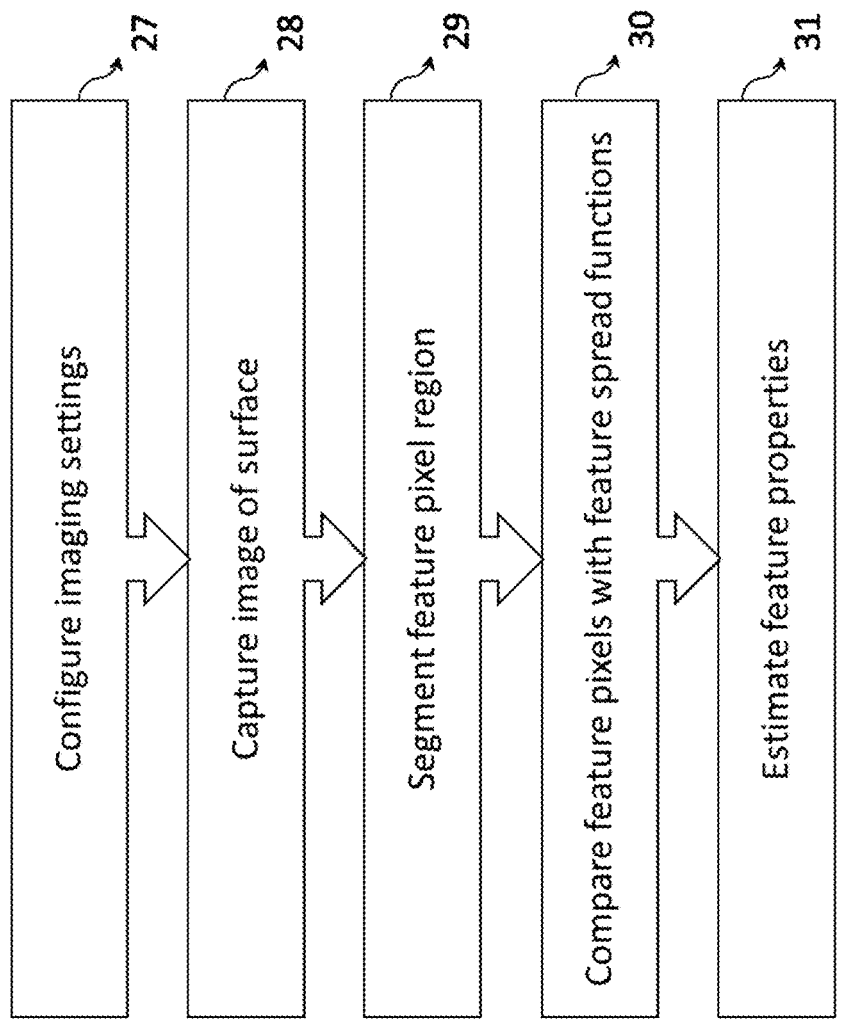
FIG. 6 shows an exemplary flow chart describing steps for recognizing a feature and estimating feature properties using feature spread functions, in accordance with the invention.

FIG. 6 shows an exemplary flow chart describing the steps for recognizing a feature and estimating feature properties using feature spread functions, in accordance with the invention. In block 27, imaging settings are configured. In some embodiments, the imaging module is set so that a focused image of surface is detected by the image sensor. In other embodiments, the imaging module is set so that a defocused image of surface is detected by the image sensor. The defocus could either be positive or negative defocus. In some embodiments, a micro-optic sensor layer is positioned between the imaging module and image sensor to facilitate phase detection. The aperture of imaging module may be configured to maximize collection of radiation from surface. In some embodiments, the aperture of imaging module is configured to minimize optical aberrations. In some embodiments, a filter is introduced in the imaging module to maximize feature sensitivity. Parameters of image sensor such as exposure time and gain are controlled to capture an image with high image quality. In block 28, one or more images are captured from the image sensor. In embodiments with a micro-optic sensor layer, the captured image is reconstructed by computing the intensity and phase of scattered radiation, and by propagating the radiation so that a desired axial plane is captured by the image. The captured image from image sensor comprises of images of features (feature pixel regions) present on surface. In block 29, one or more images of surface are processed to separate feature pixels from background pixels. In some embodiments, a focused image of surface is used for detecting feature pixels. This is because of high intensity values of feature pixels in focused images of surface. Feature pixels may be classified from their background pixels using an intensity threshold value. To minimize false positives, threshold values are designed to be higher than background pixel values. The value of a threshold may be adaptively chosen depending on pixel intensities in local neighborhood. For example, threshold value in a region with high background is higher than the threshold value in a region with lower background. In some embodiments, a focused feature may be modeled and the model shape may be correlated with image of surface. Such a correlation operation creates correlation peaks at the position of features. Correlation peaks may then be distinguished from their background using an intensity threshold value. For each feature, a feature pixel region, comprising a predetermined number of pixels that are surrounding the detected feature pixels, is segmented for estimating feature properties. In block 30, feature pixels are compared with models of feature spread functions. Feature spread functions are models of images of previously known features. They are computed from scattering models of previously known features and transfer function of said imaging module. Transfer function of imaging module includes a filter for maximizing feature detection sensitivity. The transfer function also includes optical aberrations of the imaging module. Feature pixels are compared with a number of feature spread function models and a match metric is computed between feature pixels and feature spread functions. The match metric determines if the feature corresponding to feature pixels is similar to a previously known feature. In some embodiments, a variety of scaled, rotated, and transformed feature spread functions are used for comparison. In some embodiments, previously known features used for calculating feature spread function comprises defects, including: particles, process induced defect, scratch, residue, crystal originated pit, and bumps. In some embodiments, the match metric is computed by calculating the difference between feature pixels and a feature spread function model. If the difference is larger than a predetermined match threshold, then the feature generating the feature pixels is considered to be a poor match for the feature spread function model. On the other hand, if the difference is smaller than a predetermined match threshold, then the feature generating the feature pixels is considered to be a good match for the feature spread function model. A small difference therefore leads to recognizing the feature generating feature pixels as the previously known feature corresponding to the feature spread function. In some embodiments, the comparison is performed by correlating a feature spread function model with the feature pixels. A feature spread function model is considered to be a good match to feature pixels if the correlation results in a peak. In block 31, properties of features are estimated. Properties of features include information on position, size, shape, and material composition. The position of a feature is either two dimensional or a three dimensional position on the surface. The position is estimated by localizing the position of feature pixels. In some embodiments, position is estimated by interpolating feature pixels and its corresponding feature spread function model, and by shifting the feature spread function relative to the interpolated feature pixels. Each shift is followed by computing the difference between the shifted feature spread function and the interpolated feature pixels at each shift value. The position of shift value generating the least difference is estimated as the position of feature. The size and shape of feature is estimated as the size and shape of the feature spread function model that produces the closest match (as determined by least difference or strongest correlation peak) to the feature pixels. The material composition of the feature is obtained from a map that relates the structural model of feature with material composition. The structural model of feature is obtained from the feature spread function model having the closest match with feature pixels. The structural model thus obtained is used to retrieve material properties from the map. Although structural model and material composition are independent quantities, a map between them can be constructed based on empirical data of features commonly found on surfaces.

Figure 7:
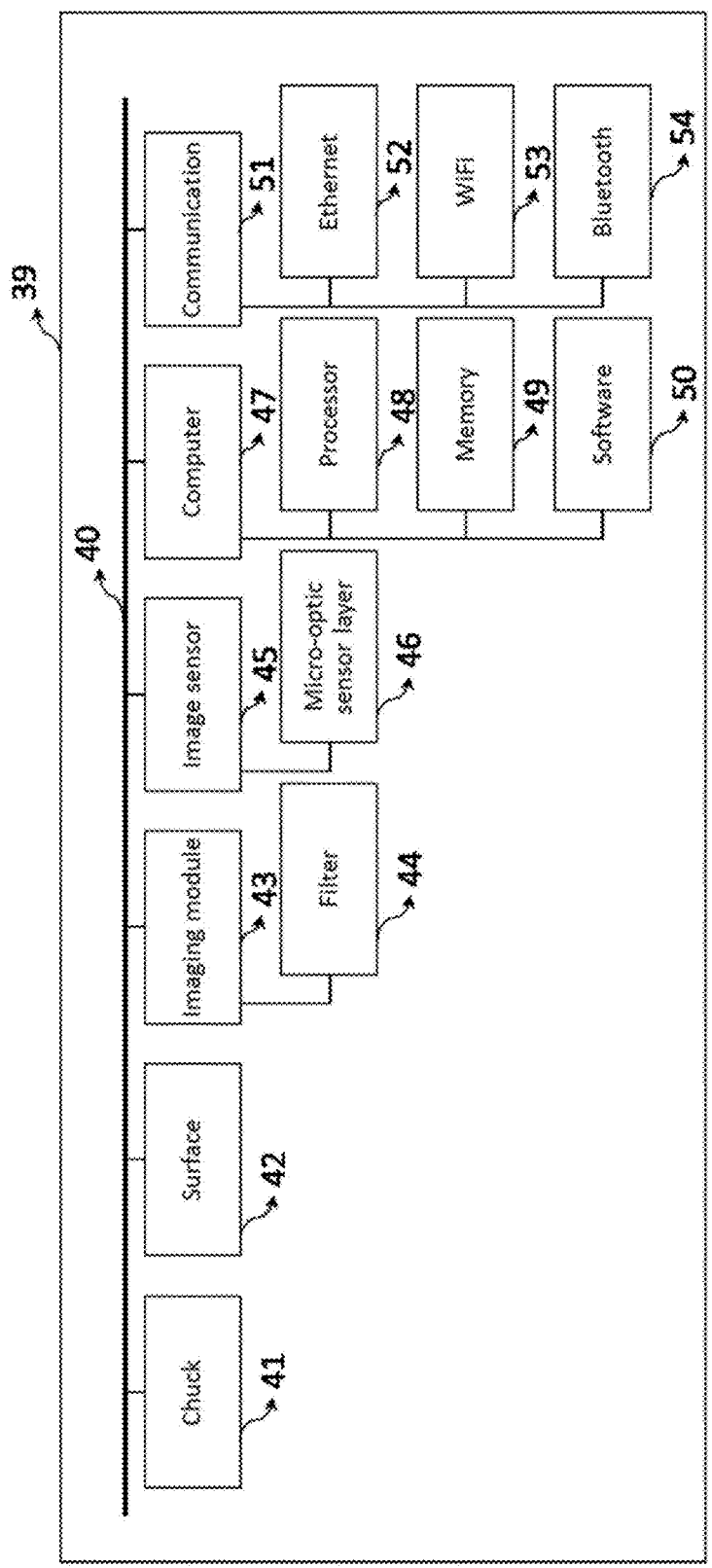
FIG. 7 shows a block diagram of a computational wafer image processing system, in accordance with the invention.

FIG. 7 illustrates a block diagram of a computational wafer image processing system, in accordance with the invention. A bus 40 connects various blocks of system 39, namely chuck 41, surface 42, imaging module 43, image sensor 45, computer 47, and communication 51. Data and control signals are carried by bus 40. Chuck 41 includes an edge handling system that holds the edge of surface, vacuum system that holds the back side of surface with vacuum suction, gas vents, and support structures used to hold surface 42 flat. Surface 42 comprises the region to be inspected by system 39. Surface 42 may be flat, curved due to gravity induced sag, or deformed due to coatings. Imaging module 43 comprises imaging optics that forms an image of surface 42 by detecting subset of scattered radiation propagating at different angles. In some embodiments, imaging module comprises a filter 44 to modulate scattered radiation incident on imaging module. Image sensor 45 captures scattered radiation from surface and transfers image data through bus 40 to computer 47. In some embodiments, image sensor 45 may include a micro-optic sensor layer 46 to facilitate phase detection. Image sensor 45 receives control information to adjust parameters such as exposure time and gain from computer through bus 40. Computer 47 includes a processor 48, memory 49, and software 50. Software 50 processes image data from image sensor 45 to compute a number of entities, including: intensity and phase profiles of electromagnetic field; computational propagation to compute image of scattered radiation; transformation from image plane to surface plane; feature pixel region; feature spread function, feature properties such as position, size, shape, and type. Software 50 generates control information and sends them through bus 40 to chuck 41, surface 42, imaging module 43, and image sensor 45. Computer 47 connects to communication block 51 for communicating data and control information through bus 40. Communication block 51 includes Ethernet 52, WiFi 53, and Bluetooth 54.

It will be recognized by those skilled in the art that various modifications may be made to the illustrated and other embodiments of the invention described above, without departing from the broad inventive scope thereof. It will be understood therefore that the invention is not limited to the particular embodiments or arrangements disclosed, but is rather intended to cover any changes, adaptations or modifications which are within the scope and spirit of the invention as defined by the appended claims.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described above, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

In the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

The above description is illustrative and is not restrictive. Many variations of the disclosure will become apparent to those skilled in the art upon review of the disclosure. The scope of the disclosure should, therefore, be determined not with reference to the above description, but instead should be determined with reference to the pending claims along with their full scope or equivalents.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

What is claimed is:

1. A method for recognizing a feature on a surface, comprising:
    acquiring an image of said feature using an imaging module and a filter to modulate electromagnetic radiation scattered from said feature, with said image of feature comprising information from multiple points of said feature;
    computing a scattering model of a previously known feature by using its shape and material composition, wherein said scattering model has computed information on electromagnetic field scattered from said previously known feature;
    computing a transfer function or point spread function of said imaging module from the properties of said imaging module and the properties of said filter;
    computing a feature spread function from said scattering model of a previously known feature and said transfer function or said point spread function of said imaging module, wherein said feature spread function represents a model of an image of said previously known feature; and
    comparing said image of feature with said feature spread function by computing a match metric between said image of feature and said feature spread function, whereby said match metric determines if said feature is similar to said previously known feature.

2. The method of claim 1, wherein said image of feature is a defocused image.

3. The method of claim 1, wherein said image of feature is a focused image.

4. The method of claim 1, wherein said scattering model of a previously known feature is computed by discretizing a structural model of said feature into a plurality of points located on a grid; computing electric field and magnetic field values at said points; and propagating said electric field to said imaging module using a near-to-far field transformation.

5. The method of claim 1, wherein said computing a feature spread function comprises multiplying said scattering model of said previously known feature with transfer function of said imaging module to generate a feature transfer function, and transforming said feature transfer function from spatial frequency domain to image domain.

6. The method of claim 1, wherein said computing a feature spread function comprises transforming said scattering model from spatial frequency domain to image domain for generating a feature response, and convolving said feature response with point spread function of said imaging module.

7. The method of claim 1, wherein said computing a match metric comprises computing the difference between said image of feature and said feature spread function.

8. The method of claim 1, wherein said computing a match metric comprises computing a correlation of said image of feature and said feature spread function.

9. A system for recognizing a feature on a surface, comprising:
    an imaging module focusing electromagnetic radiation scattered by said feature;
    a filter to modulate electromagnetic radiation scattered from said feature;
    an image sensor capturing said radiation to generate an image of said feature, with said image of feature comprising information from multiple points of said feature; and
    a processor configured to
        compute a scattering model of a previously known feature by using its shape and material composition, wherein said scattering model has information on electromagnetic field scattered from said previously known feature;
        compute a transfer function or point spread function of said imaging module from the properties of said imaging module and the properties of said filter;
        compute a feature spread function from said scattering model of a previously known feature and said transfer function or said point spread function of said imaging module, wherein said feature spread function represents a model of an image of said previously known feature;
        compare said image of feature with said feature spread function by computing a match metric of said image of feature and said feature spread function,
    whereby said match metric determines if said feature is similar to said previously known feature.

10. The system of claim 9, wherein said image sensor comprises a micro-optic sensor layer for detecting phase of said electromagnetic radiation.

11. The system of claim 9, wherein said feature is a particle.

12. The system of claim 9, wherein said feature is a process induced defect.

13. The system of claim 9, wherein said feature is a scratch.

14. The system of claim 9, wherein said feature is a residue.

15. The system of claim 9, wherein said feature is a bump.

16. The system of claim 9, wherein said feature is a crystal originated pit.

17. The system of claim 9, wherein said previously known feature comprises a scaled version of a feature.

18. The system of claim 9, wherein said previously known feature comprises a rotated version of a feature.

19. The system of claim 9, wherein said previously known feature comprises a transformed version of a feature.

\* \* \* \* \*